(12) United States Patent
Ley et al.

(10) Patent No.: US 6,361,780 B1
(45) Date of Patent: Mar. 26, 2002

(54) MICROPOROUS DRUG DELIVERY SYSTEM

(75) Inventors: Gregory R. Ley, New Brighton; Christopher Paul Knapp, Oakdale, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/190,902

(22) Filed: Nov. 12, 1998

(51) Int. Cl.[7] .................................................. A61K 9/00
(52) U.S. Cl. ........................ 424/400; 424/422; 424/423; 424/484; 424/486; 424/432; 424/443; 604/264; 604/265
(58) Field of Search ................................. 424/400, 432, 424/443, 484, 486, 422, 423; 604/264, 265

(56) References Cited

U.S. PATENT DOCUMENTS

| | | | |
|---|---|---|---|
| 3,545,439 A | * 12/1970 | Duncan | 128/260 |
| 3,857,934 A | 12/1974 | Bernstein et al. | 424/30 |
| 4,018,220 A | * 4/1977 | Emmett | 128/130 |
| 4,191,741 A | 3/1980 | Hudson et al. | 424/19 |
| 4,220,153 A | 9/1980 | Dresback | 128/260 |
| 4,581,028 A | 4/1986 | Fox, Jr. et al. | 623/2 |
| 4,596,576 A | * 6/1986 | de Nijs | 604/892 |
| 4,601,893 A | 7/1986 | Cardinal | 424/15 |
| 4,819,662 A | 4/1989 | Heil, Jr. et al. | 128/786 |
| 4,846,844 A | 7/1989 | De Leon et al. | 623/66 |
| 4,961,931 A | * 10/1990 | Wong | 424/430 |
| 5,232,444 A | 8/1993 | Just et al. | 604/96 |
| 5,269,770 A | * 12/1993 | Conway et al. | 604/265 |
| 5,844,017 A | * 12/1998 | Jamiolkowski et al. | 522/33 |
| 5,989,581 A | * 11/1999 | Groenewegen | 424/433 |

FOREIGN PATENT DOCUMENTS

| | | | |
|---|---|---|---|
| WO | 95/03083 | 7/1993 | A61M/31/00 |
| WO | 96/08286 | 9/1994 | A61M/25/00 |

\* cited by examiner

Primary Examiner—Thurman K. Page
Assistant Examiner—Liliana Di Nola-Baron
(74) Attorney, Agent, or Firm—Schwegman, Lundberg, Woessner & Kluth, P.A.

(57) ABSTRACT

A drug delivery device is described comprising a porous biocompatible solid having at least one therapeutic drug within its pores, the therapeutic drug being removable from the pores by immersion in an aqueous solution. This may also be described as a drug delivery device comprising a porous annulus comprising a biocompatible solid having at least one therapeutic drug within its pores, the therapeutic drug being removable from the pores by immersion in an aqueous solution, the annulus having a top outer surface with an outside diameter, an inner surface with an inside diameter, and a side surface, at least one of the side surface and the top outer surface having openings of the pores exposed on that surface.

The device may comprise pores having an average size of the greatest dimensions within the pores of between about $10^{-6}$ and $10^{-1}$ mm.

The device may have a medical device or component of a medical device pass through an opening in the annulus. Examples of such medical devices may include, but not be limited to medical devices or components of medical devices selected from the group consisting of catheters, tubes, and electrical leads. A catheter or electrical lead may have at least a portion of its length surrounded by the porous drug delivery device.

A more specific description of an aspect of the present invention would include a catheter or cardiac lead having a collar comprising a porous, solid material surrounding at least a length of the catheter or cardiac lead, the collar comprising a porous material selected from the group consisting of inorganic oxides, metals, polymers, and composite materials, the porous material having pores with an average greatest dimension of between about $10^{-6}$ and $10^{-1}$ mm, and the collar having a largest dimension of less than 5 mm.

16 Claims, 4 Drawing Sheets

MICROPOROUS DRUG DELIVERY SYSTEM

1. FIELD OF THE INVENTION

The present invention relates to drug delivery devices, particularly to temporary or long-term implanted drug delivery devices, and particularly to drug delivery devices which may be associated with other devices used for medical treatment.

2. BACKGROUND OF THE ART

It is known in the art that active properties can be imparted to polymeric articles by a variety of methods. One common method is to incorporate one or more activating agents into the polymeric compound during the mixing or blending phase prior to processing or manufacturing the article. Activation is accomplished by thoroughly distributing the activating agents throughout the compounding ingredients. For example, synthetic thermoplastics, natural and synthetic rubbers and other polymeric materials have been blended with activating agents such as antibacterial, antistatic, electrically conductive and other chemically or physically active agents. The activated polymeric materials are then formed into sheets, fibers, rods or other configurations by molding, casting, extruding, calendering and/or other manufacturing or processing operations.

A second method widely used to impart certain active properties to the exposed or working surface is to apply a compound containing active agents to that surface. For example, anti-fouling marine paints, antifungal sprays and coatings, fire-resistant coatings and antistatic coatings have been applied to the surface of the article. The activity of such coating is superficially skin deep and surface activity is lost to the extent that the activated coating peels or is mechanically abraded, chipped or washed away from the inactive substrate. While this method affords certain flexibility in providing an activated surface, it is at best subject to severe limitations of available range of active ingredients that can be applied in this manner and it provides limited service life and efficiency.

Another method for the production of activated articles is to expose the article to the vapors of a volatilized chemical. This ancient technique has long been applied to textiles, polymer sheets, or the like and comprises vaporizing a volatile agent, usually a biologically active agent, and then exposing the textile or other article to the vapors. A major disadvantage of this method, however, is that it requires special buildings, ventilation and recovery equipment, and safety procedures. Since the active agent has a volatilization temperature which necessarily is much lower than the melting point of the article to which the activating vapors are applied, the activation may be readily lost where the article is exposed to elevated temperatures. Thus, the treated material may be rapidly deactivated when subjected to wet or dry heat, for example, by exposure to steam sterilization or other high temperature washing procedure, intense sunlight etc.

The use of controlled release implants for administering estradiol to ruminant animals has been described in U.S. Pat. No. 4,191,741. During implantation of such implants, conditions may be unsanitary, causing infections which could lead to loss of the implant. Use of an antibiotic or germicide layer, or a coating on the surface of the implant to reduce infections and to improve implant retention has been described in U.K. Patent No. 2 136 688 A. There an antibiotic coating facilitates parenteral administration of the implants under non-sterile conditions. Requirements for cleaning any implant needle, the site of implantation, and the implantation itself are minimized or reduced. Other infection-resistant implant materials have been described in the art, such as in U.S. Pat. No. 4,581,028 which describes infection-resistant materials suitable for use as vascular graft prostheses or other implanted devices.

It is known that antimicrobial agents can be layered or coated onto the surface of an implant to inhibit infection at the site of implantation. However, some difficulties have been encountered in implementing that technology. Surface-applied antimicrobial agents have been found to be easily dislocated from the surface of the implant by nominal mechanical activity on the implants, including during packaging. Loss of antimicrobial coating reduces the activity of the treatment significantly. Coating uniformity may also be difficult to control.

U.S. Pat. No. 3,857,934 provides a method for activating nonporous polymeric articles by applying the activating agents to one surface of the article so that the agents migrate throughout the body of the article and impart an effective level of activity throughout the article and on surfaces to which the activating agent has not been applied. The articles made by this method comprise an active layer which is applied on one surface of the article, and which contains an active migrating agent. The concentration of the agent is in excess of the concentration needed to provide an effective level of activity in the layer, and is sufficient, upon migration of the agent from the layer, to impart an effective level of activity throughout the entire article. The high concentration of the active migrating agent in the layer also provides a reservoir of activating material capable of replenishing the effective surface activity of the article.

The methods and products of U.S. Pat. 3,857,934 do not require extreme processing conditions so that volatile activating agents are conveniently used at normal temperatures; toxic agents can be handled safely; and a wide variety of inactive polymers can be given almost any desired activation. Only stocks of inactive articles are needed and the desired activation may be applied when desired. The activated article has long-lasting properties which persist even if a surface layer is removed and which are replenished from the reservoir of activating agent contained within the active layer.

U.S. Pat. No. 4,819,662 describes a device referred to as a steroid lead and a process for providing medical activity through introduced chemistry in a cardiac electrode. The invention comprises an implantable cardiac pacing lead including a porous platinum electrode, a flexible electrically conductive coil, and a crimp tube coupling the electrode to the distal end of the coil. There is a recess in the crimp tube, open to the electrode at the crimp distal tube end, which houses a matrix impregnated with a therapeutic drug. The electrode itself is highly porous and may be loaded with a therapeutic drug in liquid or solid form. The drug, because of its highly porous exposure to the environment, is immediately released upon implantation of the cardiac pacing device. A variety of different matrices carrying therapeutic drugs may be housed in the recess to provide elution of different drugs and at different rates.

U.S. Pat. No. 4,846,844 describes an improved antimicrobial implant coating comprising a silicone fluid in contact with the surface of the implant and a microbial agent in contact with the silicone fluid. The silicone fluid may be first applied to the implant and the antimicrobial agent may be applied to the fluid, for example as a dust applied to the liquid coating. The effectiveness of the application is asserted to derive from the high affinity of the silicone fluid to both the implant surface and to the antimicrobial agent.

SUMMARY OF THE INVENTION

One or more drug delivery collars or annuli may be associated with a medical device such as a catheter, fixed delivery tube, electrical element (e.g., wire or casing), fixation helix, electrode or the like to provide rated delivery of one or more drugs particularly targeted for a specific or general area of the body. The microporous collar or annulus (hereinafter, generally referred to a the drug delivery element) may be sufficiently rigid that general movement of the body or organs around the collar will not bend the drug delivery element sufficiently that the openings of the drug delivery element alter so much as to dramatically change the rate of delivery of the drug(s) during the bending action.

The drug delivery element is microporous, with open pores on its exterior and at least part way through the body of the drug delivery element so that drug may elute out of the pores into the body. The drug delivery element is microporous (rather than porous) so that the drug is delivered over an extended period of time rather than immediately released into any liquid environment into which it is placed. The size of the pores, the viscosity of the liquid (or solid fill when it is wet by the environment), the physical relationship between the drug and the walls of the pores (e.g., mutually attractive, neutrally attractive, or repulsive, such as based upon their relative hydrophilicity or hydrophobicity) will assist in determining or tailoring the rate of release of the drug into the biological system into which the drug delivery element is introduced.

The drug delivery element offers simplicity in manufacture and loading of the drug into the drug delivery element. Once the porous element has been manufactured, the various drugs may be provided to the device simply by immersing the drug delivery element into a solution, dispersion, emulsion, or suspension of the drug, allowing the drug to penetrate into the pores, and then the device is dried or maintained in a desired wet state. The collar or annulus may also provide a stiffening effect to the leading edge of a catheter or lead to facilitate its positioning or movement through a patient. Collars or annular elements may also be manufactured (during the shaping of the collar or annulus) by mixing the porous matrix forming composition with the drug to be delivered, and then shaping the collar or annulus by hardening the matrix forming material in a mold or press.

DETAILED, DESCRIPTION OF THE INVENTION

Figure 1:
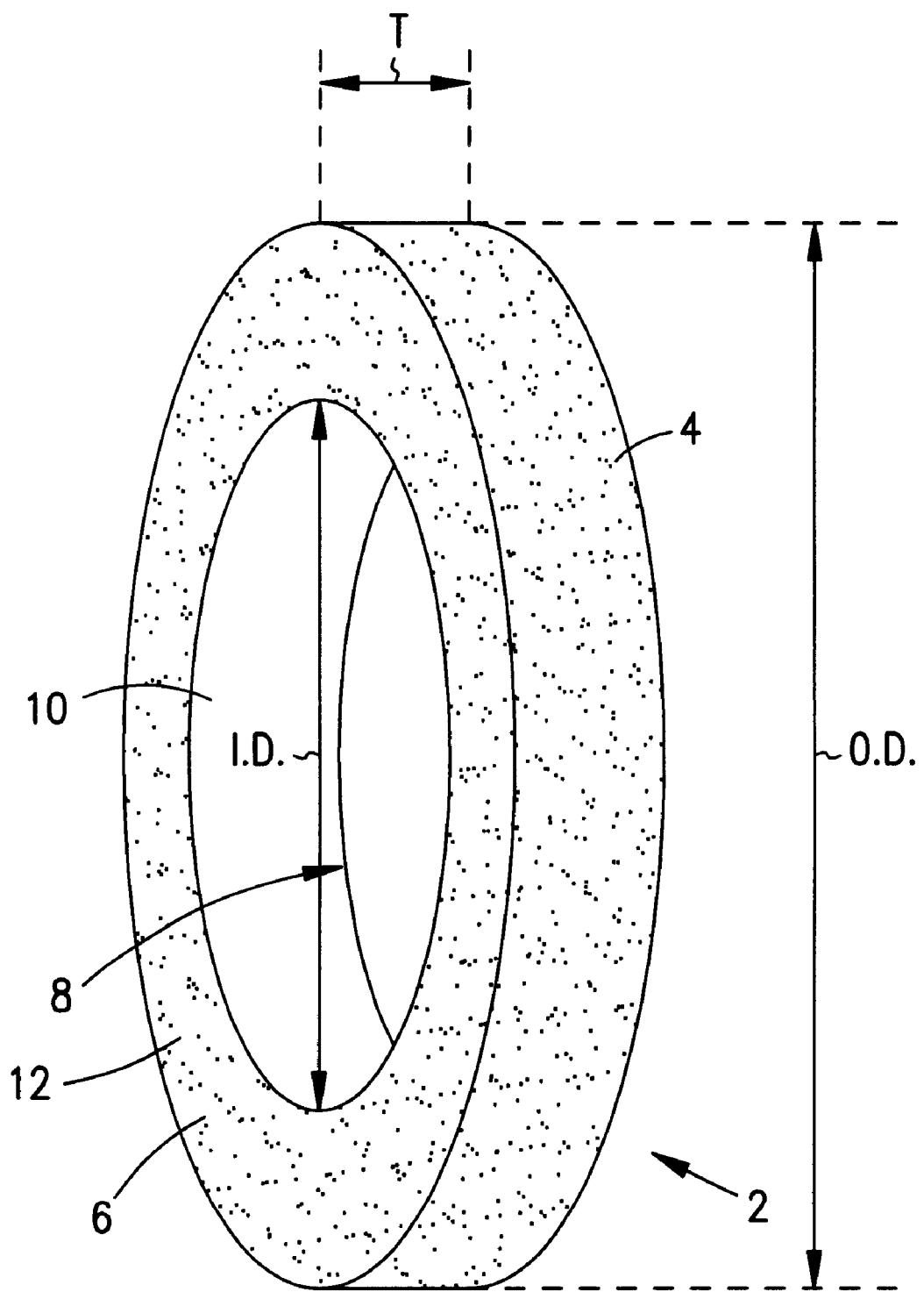
FIG. 1 shows a collar or annulus according to the present invention.

Therapeutic or prophylactic drugs are commonly provided to patients by delivery systems within the body. These systems may include pumps, bags, completely soluble systems, or materials containing drugs dissolved or suspended in a carrier, which drug elutes or more properly migrates from the carrier when it is in contact with a liquid environment. Each of these systems has its unique properties and benefits. Pumps and bags are uniquely capable of providing relatively large volumes of drug, even over fairly extended periods of time. Completely soluble systems can provide drugs from an element which can substantially eliminate itself over time by dissolving. The elution or migration delivery system can deliver very small amounts of drugs over an extended time period to a relatively small area within a patient. Alternative delivery systems are always desirable, particularly where the delivery system can be readily adapted to fixation on many different size and shape elements and where the drug delivery element can be readily manufactured.

The invention includes a drug delivery device comprising a porous biocompatible solid having at least one therapeutic drug within its pores, the therapeutic drug being removable from said pores by immersion in an aqueous solution. This may also be described as a drug delivery device comprising a porous annulus comprising a biocompatible solid having at least one therapeutic drug within its pores, the therapeutic drug being removable from the pores by immersion in an aqueous solution, the annulus having a top outer surface with an outside diameter, an inner surface with an inside diameter, and a side surface, at least one of the side surface and the top outer surface having openings of the pores exposed on that surface. The device may comprise pores having an average size of the greatest dimensions within the pores of between about $10^{-6}$ and $10^{-1}$ mm. The drug will be released in a timed manner upon contact with any bodily fluid, including blood, serum, gastric fluids, bile, saliva, and the like.

The device may have a medical device or component of a medical device pass through an opening in said annulus. Examples of such medical devices may include, but not be limited to medical devices or components of medical devices selected from the group consisting of catheters, tubes, and electrical leads. A catheter or electrical lead may have at least a portion of its length surrounded by the porous drug delivery device.

A more specific description of an aspect of the present invention would include a catheter or cardiac lead having a collar comprising a porous, solid material surrounding at least a length of said catheter or cardiac lead, said collar comprising a porous material selected from the group consisting of inorganic oxides, metals, polymers, and composite materials, said porous material having pores with an average greatest dimension of between about $10^{-6}$ and $10^{-1}$ mm, and the collar having a largest dimension of less than 5 mm.

The drug delivery element of the present invention generally comprises a microporous carrier system, the pores of which contain a therapeutic compound or composition which can be released by immersion or contact with a liquid medium. By microporous it is meant that continuous pores (e.g., in a reticulated or penetrating network of pores) do not have diameters greater than 0.1 mm. It is preferred that there be no pore diameters on the external surface of the drug delivery element which are greater than 0.1 mm, and preferably all of the pores throughout the body of the carrier of the drug delivery element are less than 0.1 mm. It is more preferred that the pore diameter of pores on the external surface be less than 0.05 mm, preferably less than 0.03 mm, more preferably less than 0.02 mm, and most preferably less than 0.01 and less than 0.005 mm. The pore diameter will depend upon a number of factors, including but not limited to the desired drug delivery rate, the solubility of drug within the expected liquid medium into which the drug delivery element will be immersed, the viscosity of any liquid drug system within the pores, the relative surface tension between the liquid drug system within the pores, the solubility or absorption rate of the drug with respect to the intended liquid medium into which it is placed, and the dimensions of the drug delivery element. It is generally found that pores greater than 0.2 micrometers, preferably pores having average diameters (or largest dimensions as they may not be perfectly round, but irregularly shaped or ovoid) of at least 0.3, at least 0.4 or at least 0.5 or 1.0 micrometers, and preferably between $10^{-6}$ and $10^{-1}$ mm or between $10^{-6}$ and $10^{-2}$ mm or between $10^{-6}$ and $10^{-6}$ mm or between $10^{-6}$ and $10^{-5}$ mm provide a suitable working range of maximum pore diameters for extended drug delivery of from a few minutes to months. The length of the collar or annulus may be within the range of whatever dimensions are tolerable within the patient, such as 0.01 mm to 5 or 10 cm.

The drug delivery element is conveniently provided as a collar or annulus which can be positioned over a conventional medical element such as a catheter, stent, electrical lead, electrode, wire, fixation helix, artificial vasculature, tube, sensing device (e.g., motion sensor, pressure sensor, etc.) and the like which is to be inserted or implanted into a patient. The collar may be premade and slid into place over the device, the collar may have a slit in it so that it can slightly open to a larger dimension to be slid over the device and then clamp slightly tighter to maintain its position, grooves may be provide on the device and a snap or pinning fixation by a bump or protuberance inside the open area of the collar may fix its position, or the collar may be molded onto the device at the desired location. The collar is desirably of sufficient rigidity that it will not bend, stretch or flex so much that its porosity greatly changes during the flexing. For example, as the collar is placed under stress, its natural response is to bend. However, when a porous element bends, the pore sizes (particularly on the surface) can distort so that the rate of release can change. When a surface bows out, for example, the rate of release will tend to increase as the pore openings on the surface will tend to expand. Useful materials for making the porous collar may be from a wide variety of biocompatible materials such as ceramics (e.g., inorganic metal oxides such as aluminum oxide, silica, zirconium oxide, titanium oxide, and composites of mixtures of inorganic oxides), metals (such as titanium, stainless steel, aluminum, and alloys), composite materials (mixtures of polymeric materials, metals, and/or inorganic oxides), and polymeric materials. It is well know within the art how to select from amongst a wide range of materials which would be useful within the practice of the present invention. The different materials would lend themselves to a variety of different manufacturing processes.

Ceramic materials can be fabricated at both room temperatures and elevated temperatures and so can be provided as both separate collars or as collars on substrates which could suffer from exposure to elevated temperatures. For example, many ceramics can be formed by solidification (dehydration) of sol-gel dispersions or suspensions of inorganic oxide particles. Other ceramics must be dehydrated and bonded together at elevated temperatures. By controlling the pressure applied to the ceramic material during hardening or fusing, the pore size can be controlled. The use of ceramic-forming particles of different average sizes will also affect the average pore size according to conventional packing and distribution laws. Metal particles may have to be fused at elevated temperatures and therefore cannot be readily formed directly on surfaces which would be adversely affected by the fusion temperature needed for metal particles. Metal particles may be bonded onto a surface with an adhesive acting to bond the particles with a particle-surface coating matrix which does not fill the pores. In fact, by proper selection of the amount (the relative amount of polymer binder to metal), the pore size can be tightly controlled and the metal/binder collars applied to a wide array of surfaces easily. Various types of polymer binders such as thermoplastic binders (applied by melting the polymer of applied from solution, dispersion, emulsion or suspension or even direct polymerization on the surface of the polymers by heat, catalysis, or radiation), thermoset binders (also provided by reaction on the surface of the particles) or by fusion of the particles (with or without additional cross linking), or the like. Amongst the useful classes of polymers would be at least included the polyamides, polyacrylates, polyurethanes, silicon polymers (e.g., polysiloxanes, silicone rubbers, siloxane graft or block polymers or copolymers, etc.), polyester resins, highly fluorinated resins (e.g., polytetrafluoroethylene), polyimides, and the like. These same classes of polymers may also comprise the mass of the drug delivery element itself. Particularly when latices are used to mold the collar or particles are fused (thermally or by solvents) to form the collar, the degree of pressure applied, the level of heat applied, the duration of the solvent, and other obvious parameters may be used to control the degree of fusion of the polymer and its degree of porosity. Porosity can also be created in polymeric materials useful for the collar by including a soluble or leachable or flowable pore-leaving component with the polymer, forming the collar, and then removing the pore-leaving component. Amongst the more well known techniques in this category is mixing a highly soluble particle (soluble in a solvent in which the polymer is not soluble), such as NaCl, into the polymer. Casting or molding the collar, and then leaching out or dissolving out the salt with water. By controlling the volume of salt, and the size of the salt particles, the pore size can be readily controlled. Alternatively, it is known to mix a non-solvent liquid from the polymer to form an emulsion or dispersion. When the polymer is solidified as a collar, the non-solvent remains as a dispersed phase which can be readily removed from the collar by washing. Thermoplastic particles may be fused under controlled pressure to form a collar with controlled pore size, as with the ceramics and the metal particles.

The various types of therapeutic drugs which may be delivered by this method include, but are not limited to anti-inflammatants, anti-arrhythmics, anti-coagulants, antibiotics, antifungal agents, steroids, enzymes, immunosuppressants, analgesics, antithrombogenic compositions, vaccine, birth control drugs, hormones, growth inhibitors, growth stimulators, and the like. Specific examples of therapeutic drugs which can be supplied in this manner as solids within the pores, solutions within the pores, emulsions within the pores, suspensions within the pores or dispersions within the pores (depending upon the form in which they may be provided) include, but are not limited to dexamethasone, dexamethasone acetate, dexamethasone sodium phosphate, cortisone, cortisone acetate, desoxycorticosterone, indomethicin, chloroquine, aspirin, acetominophen, ibuprofen, penicillin, erythromycin, cechlor, septra, vancomycin, cephalosporin, geocillin, ibutilide, heparin, warfarin, dopamine, and the like. In essence, any drug or bioactive agent which can serve a useful therapeutic or even diagnostic function when released into a patient can be used in the practice of the present invention.

These and other aspects of the present invention will be further explained with reference to the non-limiting figures and examples of the present invention. FIG. 1 shows a collar 2 of the present invention. The collar 2 has a top outer surface 4, a side surface 6 and an inner surface 8. The inner surface defines a path 10 through the collar 2. Pores 12 of various sizes and shapes are shown on the surfaces 4 and 6, but are not shown on the inner surface 8. This is done as a matter of convenience, as the inner surface 8 may have pores therein, but since that surface is likely to be flush or in tight-fitting contact with another surface, there would be minimal release from that surface. At least one surface selected from the top outer surface 4 and the side surface 6 must be porous to effect practice of the present invention. The pores 12 are preferably an intercommunicating network of pores through which fluid (including air) may pass under sustained pressure, or the pores may be concentrated at the surface of the collar 2 so that only a fast release or short-term release of the drug is effected. The size of the pores 12 through the radial depth or sideways depth of the collar 2 may be varied to effect specific release effects. It is known that the driving force for release of the drug from the surface is a combination of attraction to the liquid medium in which it is immersed or contacted and pressure from higher concentrations of the drug within the collar 12 (or carrier medium). Therefore the drug may be forced more easily into the medium if the concentration of the drug at the various release surfaces (e.g., 4 and 6) is maintained at the desired, usually high, levels. This can be accomplished easily by varying the pore size through the depth (from any surface) of the collar 2. This variation in depth can be accomplished in various fashions, such as forming the collar by layering segments with different pore sizes, using layers of particles with different diameters to form the various layers within the collar 2, or differentially applying binder at different levels of the depth so that the filled space between the particles varies through the depth. The main structural component for the collar may desirably be selected from non-electrically conductive materials from amongst the list of available materials, particularly where it is associated with leads or electrical or electronic components within the patient. Materials which are also non-magnetically responsive may also be desirable in association with other specific uses.

Figure 2:
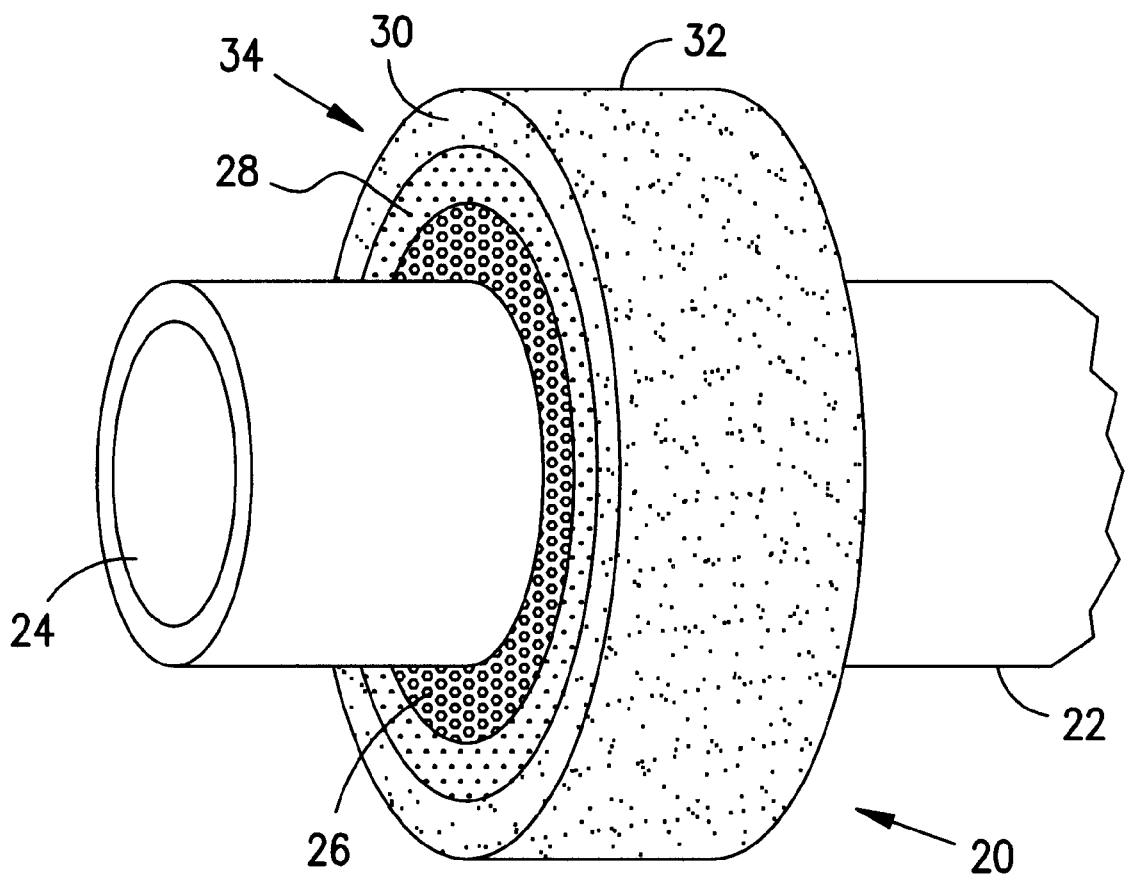
FIG. 2 shows a collar or annulus of the present invention surrounding a catheter.

FIG. 2 shows a collar 20 on a catheter 22 with a lumen 24. The collar 20 firmly surrounds the catheter 22. The side 34 of he collar 20 shows three layers 26, 28 and 30 of different pore sizes, with the largest pore sizes being closest to the catheter 22 and the smallest being farthest from the catheter 22 in layer 30. This type of pore distribution would actually be most effective where the side 34 of the collar 20 was not exposed directly to any immersion medium (e.g., a coating was present over the side 34). This would cause the concentration pressures to drive the drug within the pores from the lowest layer 26 through the middle layer 28 to the highest layer 30 to exits from the pores on the top outer surface 32. The dimensions of the collar 20 may vary dependent upon its ultimate use. Looking again at FIG. 1, the outside diameter (O.D.) Is limited only by the physical limitation of the element into a patient. A normal size range for this utility would be from about 0.5 mm to 5 mm, preferably between about 0.5 and 3 mm, more preferably between 0.5 and 1 or 2 mm. The inside diameter (I.D.) would be smaller than the O.D. and could easily range from about 0.3 or 0.4 to 4.9 mm, allowing a thickness (t) of from about 0.1 mm to 4.4 mm for the collar 2. The I.D. could also range from about 0.4 to 4.0 (or 3.9) mm, from about 0.4 to 3.0 (or 2.9) mm, or 0.4 to 2 (or 1.9) mm. The volumetric porosity of the collar may be controlled and tailored according to the ultimate use and needs of the system. Generally, however, the collar would be provided with a volumetric porosity of from about 7 to 60% by volume of pores, more likely from about 10 to 40% volume of pores in the collar 2, and more narrowly as from 15 to 35% by volume of pores in the collar 2. A specific example of a collar made according to the present invention was a ceramic collar comprising inorganic oxides ($\geq$99.5% Aluminum oxide) with a 20–25% volumetric porosity, having a length of 0.040 inches (0.11 cm), and internal diameter of 0.060 inches (0.16 cm), and an external diameter of 0.090 inches (0.24 cm) formed by firing the aluminum oxide at 1000° C. under controlled pressure. The average pore size was measured at about 1 to 5 microns or between $1\times10^{-3}$ and $5\times10^{-3}$ mm. The collar was immersed in an aqueous solution of dexamethasone acetate for a few minutes and then removed and dried in a sterile environment. The dried collar was then immersed in water and the dextramethasone acetate was removed from the pores over time. This steroid could be used in vivo with a catheter or lead because of the biocompatible composition of the collar material (the aluminium oxide) and the use fulness of dexamethasone acetate as a delivered drug. The pores made by the particular method of this example extended only 10 micrometers in depth from the top outer surface of the collar, which was sufficient for release of the drug according to the present invention. Fifteen samples of this type of collar were tested for levels of loading with dexamethasone acetate and the data is shown in the following table.

| Sample Number | Collar Weight (mg) | Collar/Drug Wt. (Mg) | Drug Wt. (Mg) |
| --- | --- | --- | --- |
| 1 | 8.36 | 8.45 | 0.09 |
| 2 | 8.30 | 8.43 | 0.13 |
| 3 | 8.33 | 8.46 | 0.13 |
| 4 | 8.09 | 8.36 | 0.27 |
| 5* | 8.15 | 8.29 | 0.14 |
| 6* | 8.22 | 8.33 | 0.11 |
| 7 | 8.24 | 8.48 | 0.24 |
| 8 | 8.15 | 8.66 | 0.51 |
| 9 | 8.37 | 8.52 | 0.15 |
| 10 | 8.28 | 8.44 | 0.16 |
| 11 | 8.39 | 8.53 | 0.14 |
| 12* | 8.37 | 8.49 | 0.12 |
| 13 | 8.16 | 8.51 | 0.35 |
| 14 | 8.16 | 8.48 | 0.32 |
| 15 | 8.18 | 8.39 | 0.21 |

Figure 3:
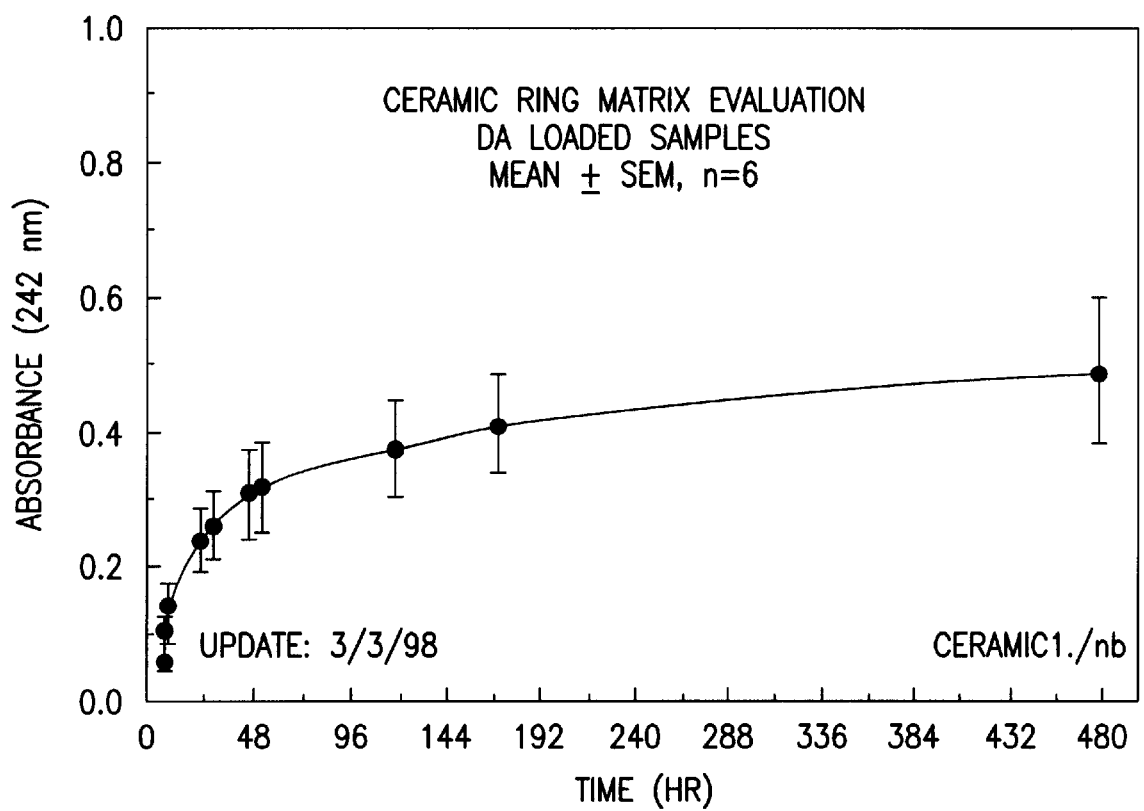
FIG. 3 is a graph of radiation absorption (at 242 nm) versus time to measure the elution of dexamethasone acetate.
Figure 4:
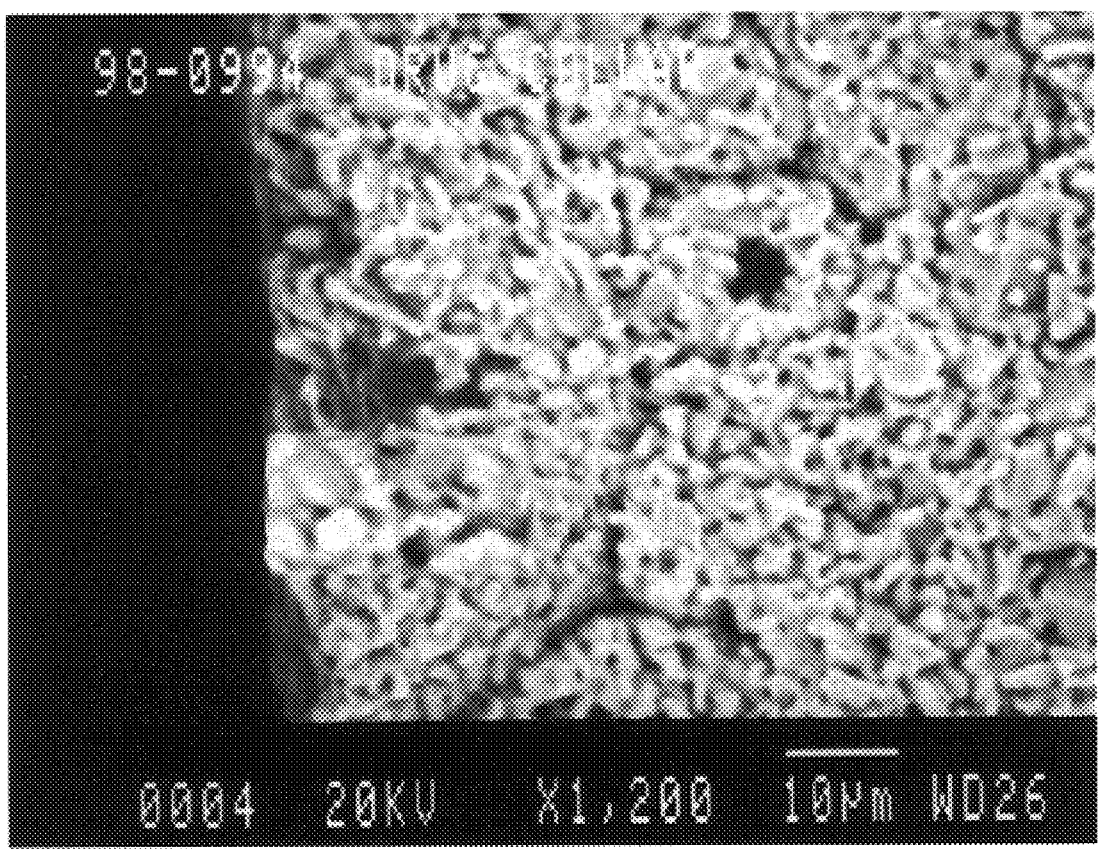
FIG. 4 is a copy of an SEM of the surface pore structure of a ceramic collar or annulus according to one aspect of the present invention.

* denotes the use of an approximation during the calculation of values. The collars were loaded with 25% by weight dexamethasone acetate in ethanol. A vacuum was applied to the dry collars to remove air from the pores and the collars soaked for twenty minutes in the ethanol solution. The soaked collars were then dried for three hours and the delivered for elution testing. Elution testing was done by in vitro testing of the light absorption of a solution into which the collars were placed. The absorption at 242 nm was measured (a wavelength at which dexamethasone acetate strongly absorbs) and the release of the drug noted by increasing levels of absorbance, as shown in FIG. 3. The SEM of FIG. 4 clearly shows the interpenetrating nature of the porosity of the ceramic material. Pore size would be estimated by taking the largest linear dimensions within each of the open areas and using that linear value as the largest dimension for that pore.

The rate of release from the collars is intended to be highly tailored to the specific ultimate use intended for the catheter or lead. The leads which may be used include traditional leads such as cardiac leads, but may also include other leads such as leads to organs that produce enzymes and hormones (as in the electrically stimulated treatment for Parkinsonism to accelerate the natural production of L-dopa), in stimulating breathing (in the prevention of SIDS or control of sleep apnea), neurological leads, hearing related leads, tinitus suppression leads, and the like. It is preferred that release be initiated in less than five hours (preferably less than 1 or 2 hours) and that release continue in medicinally significant amounts for more than 24 or more than 48 hours. The term medicinally significant amount has clear meaning to those in the medical field and relates to the ability of the amount of drug being released to sustain the medical or biological effect initiated by the release of the drug or maintain a therapeutic or prophylactic condition in a region of the patient. As shown in FIG. 3, the drug delivery system of the present invention has been able to establish and maintain the release of a medicinally significant amount for more than 360 hours without significant attempts at optimizing the release rate for the specific drug or the media within which the carrier was provided.

The structure of the collar or annulus may be altered to control the elution rate or release rate of the drug. For example, the size of the pores on the outer surface which is exposed to the body liquids is probably one of the most significant rate limiting factors in the design of the system, while at the same time, the pore size controls the amount of liquid which can be retained within the collar or annulus. As the pore size increases internally, larger amounts of drug may be stored, while larger pore sizes on the surface increase the drug release rate. A good design would therefore have pore openings on the surface of the collar or annulus with smaller average diameters of the pores than larger pores within the body of the collar or annulus which are fluid transferring connected to the pores on the surface of the collar or annulus. It is preferred that the interior pores have average pore dimensions which are at least 10%, preferably at least 20% and more preferably at least 50% greater in average diameter than the pores open at the surface of the collar or annulus. Pore size is estimated or calculated in networked systems or reticulated systems such as those shown in FIG. 4 by drawing virtual circles within each pore opening, so that an estimated diameter of the pore, equal to the size of the largest circle which includes all of the pore area, but no more than 30% and preferably no more than 25% or no more than 20% of volume of mass surrounding the pore being included within the area measurement of the circle defining the average pore size. Circles may be aligned within the pores to virtually capture the open area within the collar or annulus. Pore size is also typically determined from cross-sections of the materials (the surface being, in effect, a natural cross-section).

The collar or annulus does not have to be a continuous circle. For example, there may be a separation within the circumference of the collar to allow the collar to open slightly so that it may be engaged with a catheter or tube without excessive size tolerance requirements. In fact, the slightly flexing action of such an opened collar would allow the collar to perform a clamping action on the catheter of lead as the elastic nature of the collar closed the opened gap after the collar was placed onto the electrical lead, catheter, tube, or cardiac pacing lead. There may be screw threads on the collar to assist in advancement of placement of the collar or annulus or the attached medical device.

What is claimed:

1. A drug delivery device comprising a rigid porous biocompatible solid in the shape of a collar or annulus having an exterior surface that defines an opening therethrough, and a medical device having an outer surface where the outer surface of the medical device passes through the opening and is fixed to the rigid porous biocompatible solid, and where the rigid porous biocompatible has at least one therapeutic drug within its pores, said therapeutic drug being removable from said pores by immersion in an aqueous solution.

2. The device of claim 1 wherein said pores have an average size of between $10^{-6}$ and $10^{-1}$ nm.

3. The device of claim 1 wherein said pores have an average size of between about $10^{-6}$ and $10^{-3}$ mm.

4. The device of claim 1 wherein said medical device or component of a medical device is selected from the group consisting of catheters, tubes, and electrical leads.

5. A catheter or electrical lead having at least a portion of its length surrounded by the device of claim 1.

6. A catheter or cardiac lead having a collar comprising a rigid, porous, solid material surrounding at least a length of said catheter or cardiac lead.

7. The drug delivery device of claim 1, where the rigid porous biocompatible solid is a ceramic.

8. The drug delivery device of claim 1, where the rigid porous biocompatible solid is a metal.

9. The drug delivery device of claim 1, where the rigid porous biocompatible solid is a polymer.

10. The drug delivery device of claim 1, where the rigid porous biocompatible solid is a composite material.

11. The catheter or cardiac lead of claim 6, wherein the porous, solid material includes pores with an average greatest dimension of between about $10^{-6}$ and $10^{-1}$ mm.

12. The catheter or cardiac lead of claim 6, where the porous, solid material is an inorganic oxide.

13. The catheter or cardiac lead of claim 6, where the porous, solid material is a metal.

14. The catheter or cardiac lead of claim 6, there the porous, solid material is a polymer.

15. The catheter or cardiac lead of claim 6, where the porous, solid material is a composite material.

16. The catheter or cardiac lead of claim 6, where the collar has a largest dimension of less than 5 mm.

* * * * *